US007574922B2

(12) United States Patent
Doleski et al.

(10) Patent No.: US 7,574,922 B2
(45) Date of Patent: Aug. 18, 2009

(54) TEST APPARATUS TO DETERMINE THE SHEAR STRENGTH OF A COMPOSITE SANDWICH BEAM UNDER A HIGH HYDROSTATIC LOAD

(75) Inventors: Robert F. Doleski, Middletown, RI (US); Stanley J. Olson, Newport, RI (US); Stephen F. Oliver, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 160 days.

(21) Appl. No.: 11/776,776

(22) Filed: Jul. 12, 2007

(65) Prior Publication Data

US 2009/0013796 A1    Jan. 15, 2009

(51) Int. Cl.
*G01N 3/24* (2006.01)
(52) U.S. Cl. ........................................................ 73/841
(58) Field of Classification Search ................... 73/842, 73/841
See application file for complete search history.

(56) References Cited

U.S. PATENT DOCUMENTS

| 3,622,035 | A | * | 11/1971 | Suter ........................... 280/834 |
| 3,728,895 | A | | 4/1973 | Shaw |
| 3,847,182 | A | * | 11/1974 | Greer ........................... 138/30 |
| 3,911,735 | A | | 10/1975 | Di Crispino |
| 4,432,388 | A | * | 2/1984 | Rest ........................... 137/403 |
| 4,607,532 | A | | 8/1986 | Arthur et al. |
| 5,266,137 | A | * | 11/1993 | Hollingsworth ............. 156/156 |
| 5,431,061 | A | | 7/1995 | Bertelsen et al. |
| 5,493,898 | A | | 2/1996 | Bilkhu et al. |
| 5,954,696 | A | * | 9/1999 | Ryan ........................... 604/141 |
| 5,993,066 | A | * | 11/1999 | Leuthold et al. ............ 384/113 |
| 6,691,580 | B1 | | 2/2004 | Bertelsen |
| 7,469,800 | B2 | * | 12/2008 | Elstone et al. ................. 222/1 |

* cited by examiner

*Primary Examiner*—Lisa M Caputo
*Assistant Examiner*—Octavia Davis
(74) *Attorney, Agent, or Firm*—James M. Kasischke; Michael P. Stanley; Jean-Paul A. Nasser

(57) ABSTRACT

An apparatus for determining the strength of composite sandwich beam in which an enclosure and insertable bladder is provided. The apparatus comprises positioning a bladder within the enclosure. The beam to be tested is slid through a cutout or aperture of the enclosure with support feet holding the beam in place within the enclosure. The enclosure supports the bladder sides with one face of the bladder pressuring the composite sandwich beam. For testing, water is pumped under pressure through a fitting into the bladder. The tolerances between the beam, enclosure and an extrusion seal do not allow the bladder to squeeze outward with the result being measurable testing pressure on the face of the composite beam.

20 Claims, 14 Drawing Sheets

TEST APPARATUS TO DETERMINE THE SHEAR STRENGTH OF A COMPOSITE SANDWICH BEAM UNDER A HIGH HYDROSTATIC LOAD

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to an apparatus and method of use for determining the shear strength of a composite sandwich beam using measurable hydrostatic loads.

(2) Description of the Prior Art

A composite sandwich is a load bearing structure that typically has thin but stiff face sheets and a lightweight but soft core. This type of structure offers an excellent strength to weight ratio. For this reason, composite sandwiches are increasingly considered for use in naval structures such as boat hulls and pressure vessels (i.e., launch canisters and torpedo tubes).

When a composite sandwich is loaded with a force normal to the face sheet, the core is loaded in shear. Failure of the core in shear is a prevalent failure mode of composite sandwiches.

The historical method of testing the shear strength of a composite sandwich is to test a composite beam in a three or four point bend. The three or four point bend test method creates stress concentrations under the loading points. These stress concentrations would not be located in a real world situation when a sandwich panel would be loaded under a hydrostatic load. Also, the stress concentrations can cause premature failure of the composite sandwich panel. This failure is particularly true in cases where the core material is brittle or very soft.

As such, a need exists for loading over the face or faces of a composite sandwich panel or beam such that stress concentrations of loading can be eliminated or reduced when a shear strength test is conducted on the composite sandwich beam.

SUMMARY OF THE INVENTION

It is therefore a general purpose and primary object of the present invention to provide a device and a method of testing the shear strength of a composite sandwich beam with a hydrostatic load.

It is a further object of the present invention to provide a device and method of testing the shear strength of a composite sandwich beam such that stress concentrations of loading can be eliminated or reduced.

To attain the objects described, there is provided a test apparatus including a rubber bladder positioned and sized to fit inside an enclosure. The composite sandwich beam to be tested is slid through a cutout of the box enclosure. At least two pins are slid and fit to hold at least two feet in place at an end of the box enclosure. The feet act as a support platform to hold the composite sandwich beam within the box enclosure during hydrostatic testing.

With the composite sandwich beam resting on the feet, there is only a small amount of clearance between the composite sandwich beam, the sides of the enclosure and top of the cutouts. As such, the enclosure supports the sides of the bladder with an end of the bladder pressuring the composite sandwich beam.

To load for hydrostatic testing, water or an alternate fluid is pumped under pressure through a pressure fitting into the bladder. The tight tolerances between the composite sandwich beam, the box enclosure and an optional extrusion seal do not allow the bladder to extrude with the result being hydrostatic pressure on the face of the composite sandwich beam.

The hydrostatic pressure can be increased, decreased or cycled at the pressure fitting to predetermined levels suitable for testing the composite sandwich beam. Heating and cooling can also be applied to the test apparatus and test composite sandwich beam at predetermined levels.

As stated above, the feet provide support to the composite sandwich beam and minimize the stress concentrations on the surface and at the end of the composite sandwich beam. The feet are permitted to rotate on positioning pins to remain tangent to the surface of the composite sandwich beam as the beam bends. The adjustable feet even permit testing of a composite sandwich beam that is tapered in thickness.

An advantage of the present invention is that high pressures can be obtained with the test apparatus by the use of the pressure fitting. The ability to test to high pressures is necessary when characterizing systems used in undersea applications. The apparatus could conceivably be designed for operational testing pressures as high as nominally 4500 pounds per square foot plus any desired test beam safety factors.

BRIEF DESCRIPTION OF THE DRAWINGS

Other objects, features and advantages of the present invention will become apparent upon reference to the following description of the preferred embodiments and to the drawings wherein.

DETAILED DESCRIPTION OF THE INVENTION

Figure 1:
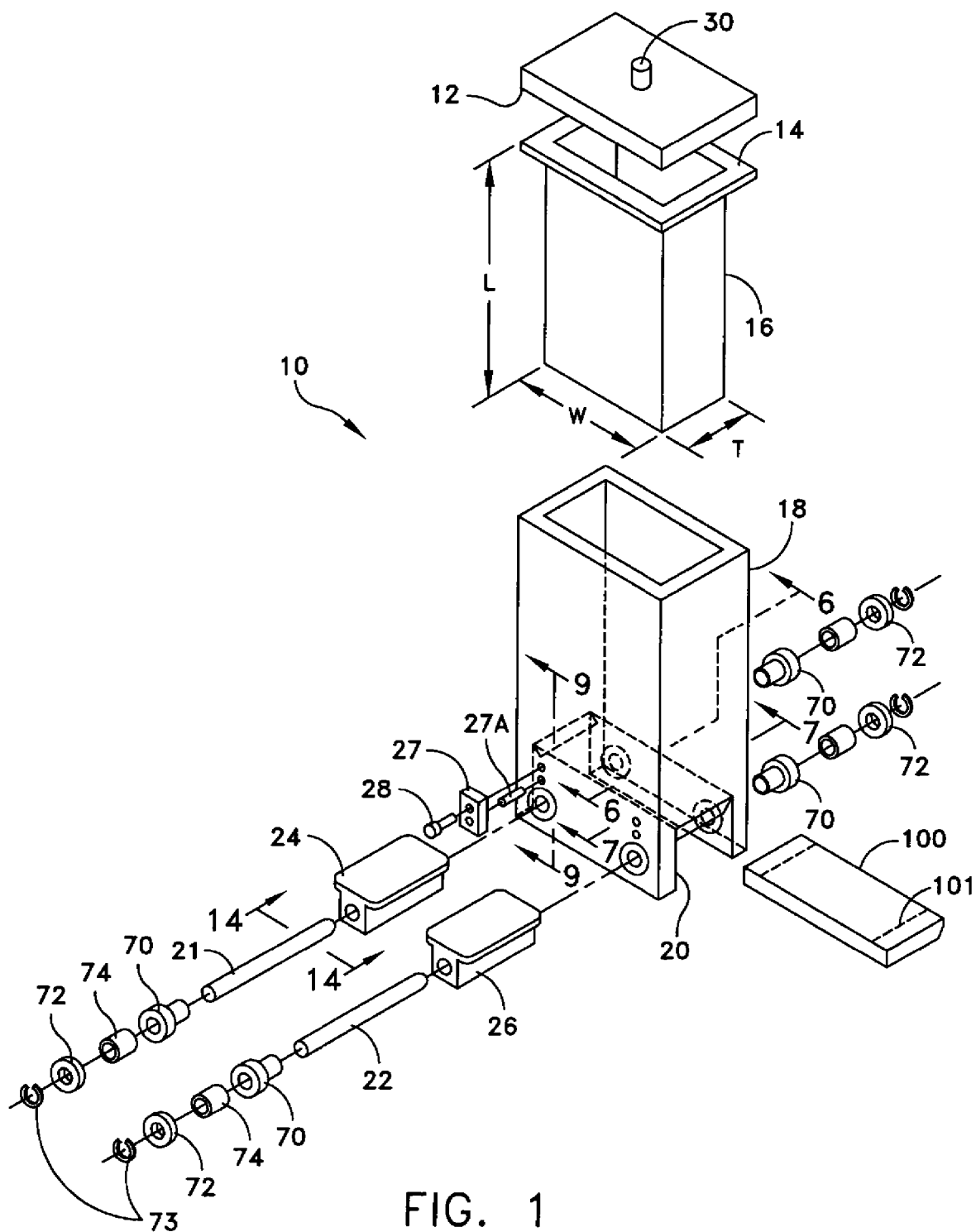
FIG. 1 depicts the test apparatus of the present invention with a detailed view of a vernier bushing used with the positioning pins removed for purposes of clarification.

A more complete understanding of the invention and many of the attendant advantages thereto will be readily appreciated as the same becomes better understood by reference to the following detailed description when considered in conjunction with the accompanying drawings wherein like reference numerals and symbols designate identical and corresponding parts throughout several views and wherein a test apparatus 10 of the present invention is primarily depicted in FIG. 1, with variants and optional equipment depicted in subsequent figures as described below.

In FIG. 1 and during assembly for testing, a top plate 12 is positioned to sandwich a flange 14 of a rubber or elastomeric bladder 16 against the lip of a box enclosure 18 forming a seal between both. The assembly of the top plate 12 to the box enclosure 18 is by bolting, clamping together or fastening by any mechanical means known to those skilled in the art.

The bladder 16 is sized to fit inside of the box enclosure 18. The length (L) of the bladder 16 is optimally sized with the width (W) and thickness (T) to similar dimensions of testable composite sandwich beams. The flange 14 or sealing lip of the bladder 16 may be further restrained to prevent extruding under testing pressure.

Additionally, the box enclosure 18 may be substituted with any enclosure suitable for accommodating the bladder 16. Variants of the enclosures used for the apparatus 10 are depicted in FIGS. 2, 3 and 4.

Figure 2:
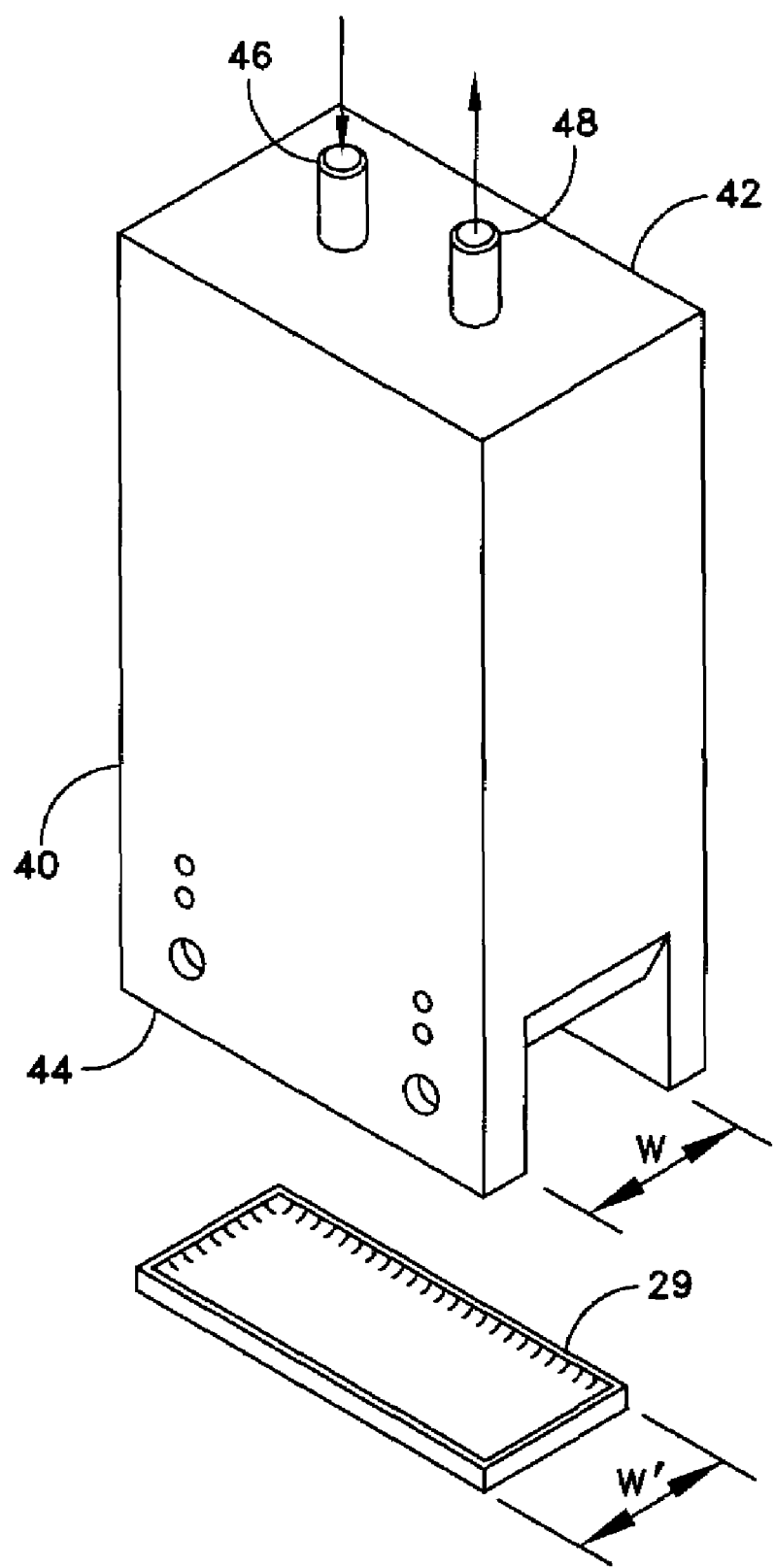
FIG. 2 depicts a first variant of the enclosure of the present invention with the composite sandwich beam removed for clarification.

In a first variant, depicted in FIG. 2, a box enclosure 40 utilizes an integrated top plate 42. The bladder 16 is inserted from an opposite open end 44 or bottom of the box enclosure 40. The bladder 16 fluidly connects to a pressure fitting 46 and a relief/drain fitting 48. The fluid flow to and from pressure fitting 46 and the relief/drain fitting 48 is controlled by shutoff valves (not shown) or by other control mechanisms known to these skilled in the art. The relief/drain fitting 48 may include tubing (not shown) that extends to a small distance above a bottom or opposite end of the interior of the bladder 16.

Figure 3:
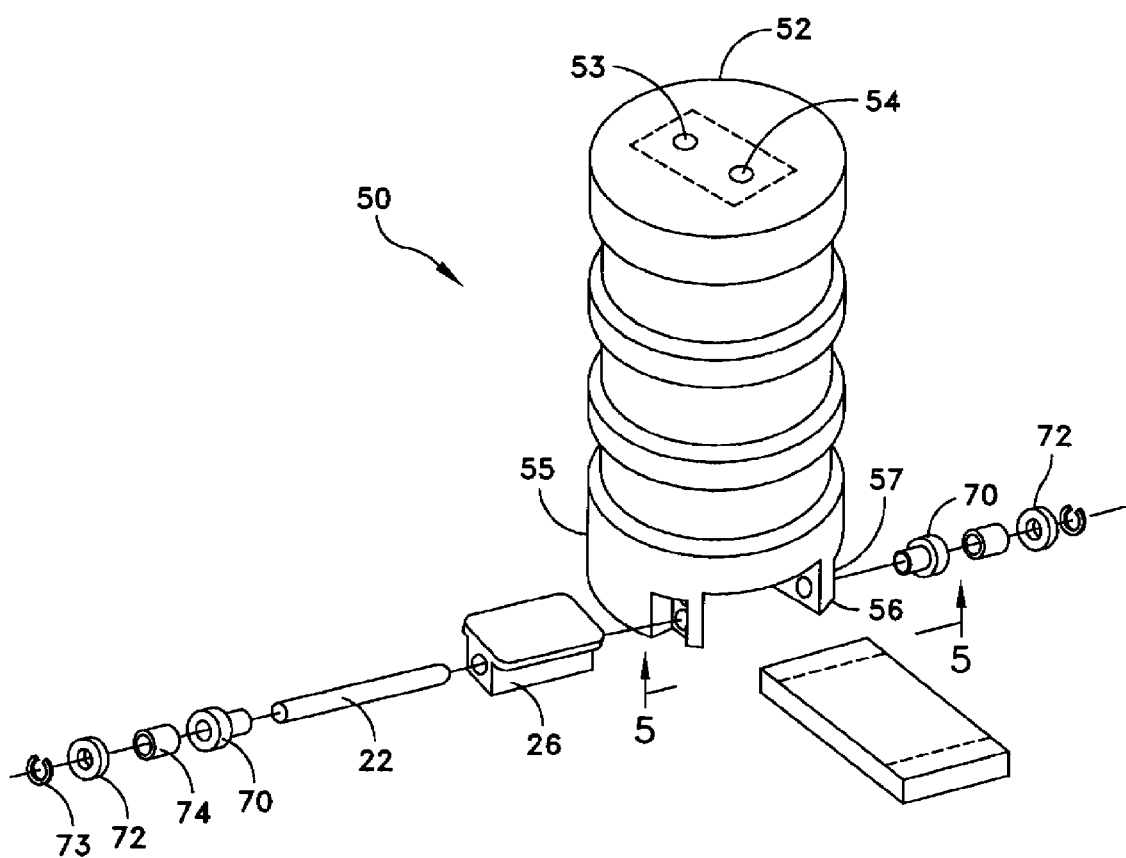
FIG. 3 depicts a second variant of the enclosure of the present invention.
Figure 4:
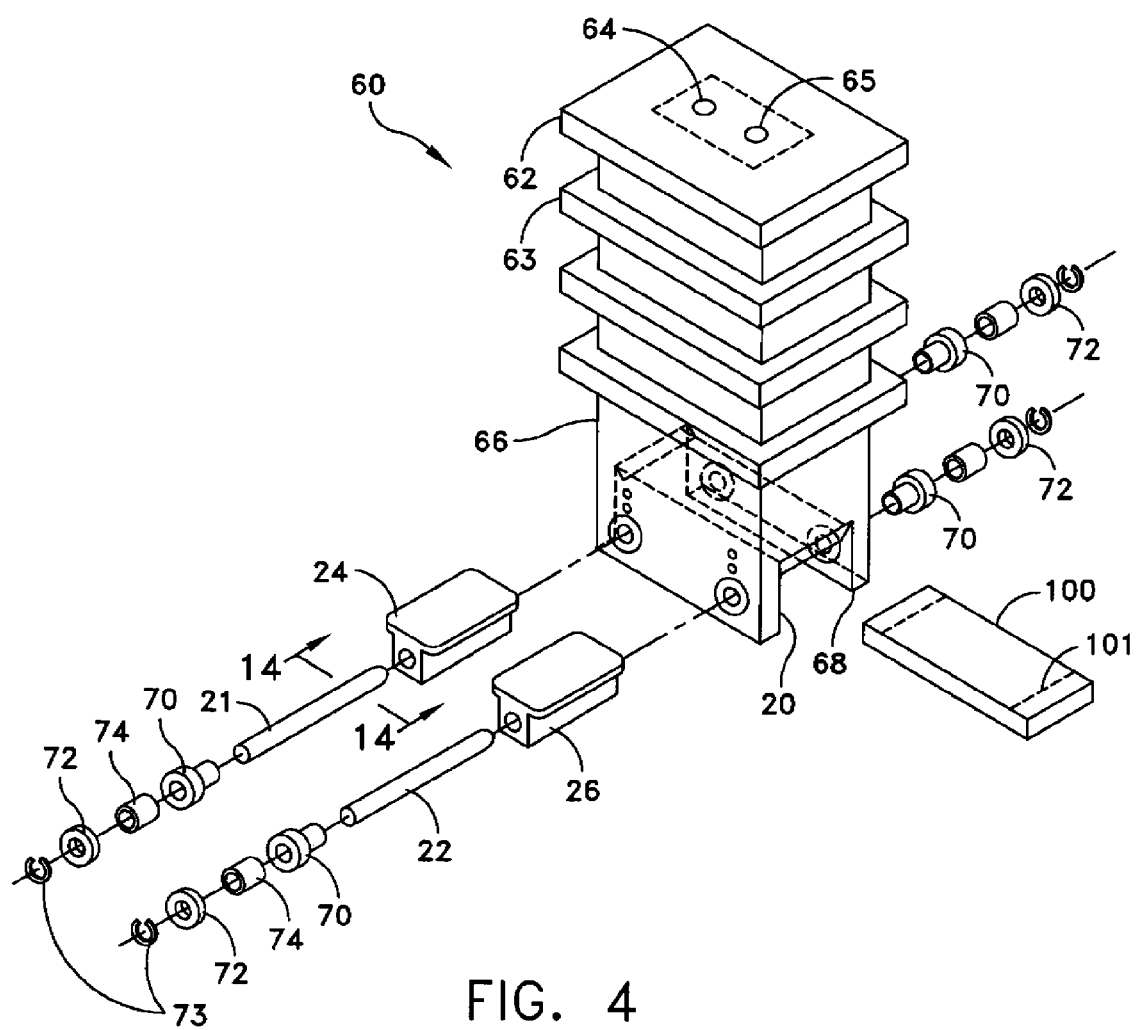
FIG. 4 depicts a third variant of the enclosure of the present invention.

A second and third variant of the box enclosures, shown in FIG. 3 and FIG. 4, are reinforced versions of the box enclosure with thickened sections encompassing the box enclosure.

Figure 5:
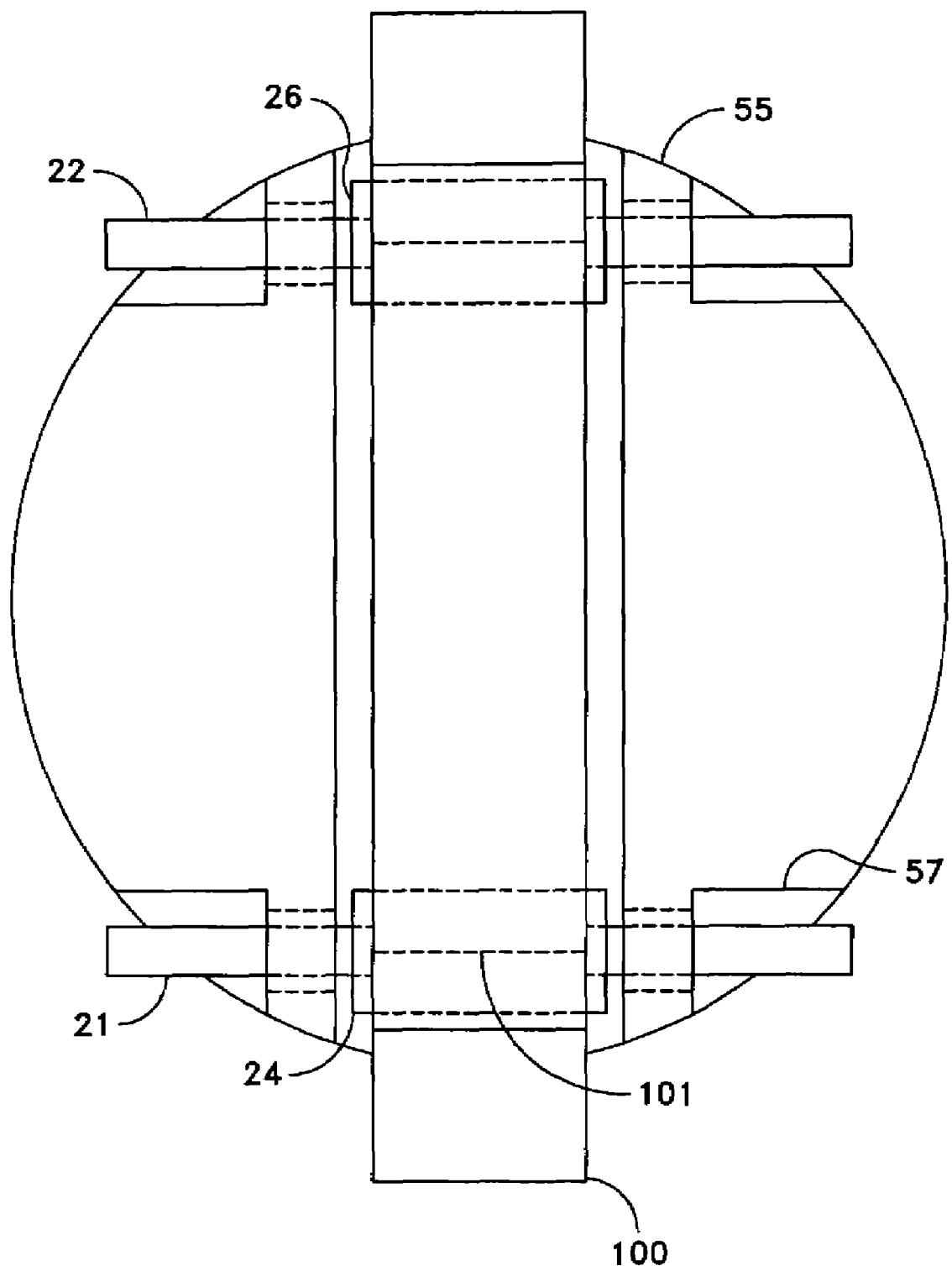
FIG. 5 depicts a plan view of the second variant of the enclosure of the present invention with the view taken along with reference line 5-5 of FIG. 3.

The second variant enclosure 50 is shown in FIG. 3 with an alternate view shown in FIG. 5. In the figure, the enclosure 50 is tubular along a longitudinal axis. A top or first section 52 is made of thickened material with a pressure fitting 53 and a relief/drain fitting 54 positioned therethrough. Similarly, a bottom section 55 is made of thickened material around a cutout 56. Recesses 57 are positioned in the cutout 56.

The third variant enclosure 60 is shown in FIG. 4. A top or first section 62 is made of thickened material with thickened reinforcement supports 63 encompassing the enclosure along a longitudinal axis of the enclosure. The top section 62 includes a pressure fitting 64 and a relief/drain fitting 65. Similar to the top section 62, a bottom section 66 is made of sufficiently thickened material around a cutout 68.

Using FIG. 1 as an example for testing using the box enclosure 18, a composite sandwich beam 100 to be tested is slid through a cutout 20 at the bottom end of the box enclosure 18. The composite sandwich beam 100 can have an excess length beyond a dotted enclosure contact 101 in order to ease positioning of the composite sandwich beam within the box enclosure 18 and to provide sufficient overhang. At least two pins 21 and 22 are slid and fit to hold at least two feet 24 and 26 in place at the bottom of the box enclosure 18. The feet 24 and 26 act as a support platform to hold the composite sandwich beam 100 within the box enclosure 18 for hydrostatic testing.

The pins 21 and 22 may be substituted by any fixtures known to those skilled in the art. The feet 24 and 26 are allowed to pivot slightly on the pins 21 and 22. The feet 24 and 26 are rounded off with a camber and coated with an anti-friction material for smooth distributed contact with the loaded composite sandwich beam 100, and comparatively easy movement of the composite sandwich beam in and out of the box enclosure 18.

With the composite sandwich beam 100 resting on the feet 24 and 26, there is only a small amount of clearance between the composite sandwich beam, the sides of the box enclosure 18 and top of the cutout 20. As such, the box enclosure 18 supports the sides of the bladder 16 with the bottom of the bladder pressuring an optional flexible extrusion seal 29 (shown in FIG. 2) and the composite sandwich beam 100.

To load for hydrostatic testing, water is pumped under pressure through a pressure fitting 30 fluidly connecting to the bladder 16. The water pressure is measured as part of determining the strength of the composite sandwich beam 100. The hydrostatic pressure can be increased or decreased at the pressure/drain fitting 30 to predetermined levels suitable for testing the composite sandwich beam 100. Once testing is complete, the pressure fitting 30 may also be used to drain and de-pressurize the bladder 16.

The tight tolerances between the composite sandwich beam 100 and the box enclosure 18 do not allow the bladder 16 to squeeze outward with the result being hydrostatic pressure on the extrusion seal 29 and on the face of the composite sandwich beam 100.

As stated above, the feet 24 and 26 provide support to the composite sandwich beam 100 and reduce the stress concentrations at the end of the composite sandwich beam. The stress concentrations can be completely eliminated in the most important area, which is the middle of the composite sandwich beam 100. The middle of the composite sandwich beam 100 is where a failure would likely occur.

An advantage of the present invention is that very high pressures can be obtained with the test apparatus 10 by the use of the pressure fittings 30, 46, 53 and 64. The ability to test to high pressures is necessary when characterizing systems used in undersea applications.

A variety of materials, shapes and sizes can be used for the basic components described above. As described further below, positioning of the pins 21 and 22 can be made adjustable so that the support feet 24 and 26 and therefore the thickness of the composite sandwich beam 100 can be varied. These adjustments allow a plurality of beams to be properly positioned in the box enclosure 18.

The side walls of the box enclosure 18 can also be made adjustable for the same reasons. Shims can also be used for the purpose of adjusting the size of the bladder 16 within the box enclosure 18 to fit composite sandwich beams of various widths.

The pins 21, 22 and the feet 24, 26 may be used on the variants of the box enclosure 18. In FIG. 3 and the alternate view of FIG. 5, the composite sandwich beam 100 to be tested is slid through a cutout 56. The pins 21 and 22 are slid into the recesses 57 and fit to hold the feet 24 and 26 in place at the bottom of the enclosure 50. The feet 24 and 26 act as a support platform to hold the composite sandwich beam 100 within the enclosure 50 for hydrostatic testing of the composite sandwich beam.

The composite sandwich beam 100 rests on the feet 24 and 26 with only a small amount of clearance between the composite sandwich beam, the sides of the box enclosure 50 and top of the cutouts 56. As such, the box enclosure 50 supports the sides of the bladder 16 with the bottom of the bladder pressuring the composite sandwich beam 100 and the extrusion seal 29 (shown in FIG. 2). The perimeter of the extrusion seal 29 may be formed or manufactured to conform to the cutout 56 by means recognizable to those skilled in the art.

To load for hydrostatic testing, water is supplied under pressure through a pressure fitting 53 fluidly connecting to the bladder 16. The tight tolerances between the composite sandwich beam 100 and the enclosure 50 do not allow the bladder 16 to squeeze outward with the result being hydrostatic pressure on the extrusion seal 29 (See FIG. 2) and on the face of the composite sandwich beam. The hydrostatic pressure can be increased or decreased at the pressure fitting 53 to predetermined levels suitable for testing the composite sandwich beam 100.

In FIG. 4, the composite sandwich beam 100 to be tested is slid through a cutout 68. The pins 21 and 22 are slid and fit to hold the feet 24 and 26 in place at the bottom of the enclosure 60. The feet 24 and 26 act as a support platform to hold the composite sandwich beam 100 within the enclosure 60 for hydrostatic testing.

To load for hydrostatic testing, water is supplied under pressure through a pressure fitting 64 fluidly connecting to the bladder 16. The tight tolerances between the composite sandwich beam 100 and the enclosure 60 do not allow the bladder 16 to squeeze outward with the result being hydrostatic pressure on the extrusion seal 29 (See FIG. 2) and on the face of the composite sandwich beam 100. The hydrostatic pressure can be increased or decreased at the pressure fitting 64 to predetermined levels suitable for testing the composite sandwich beam 100.

Figure 6:
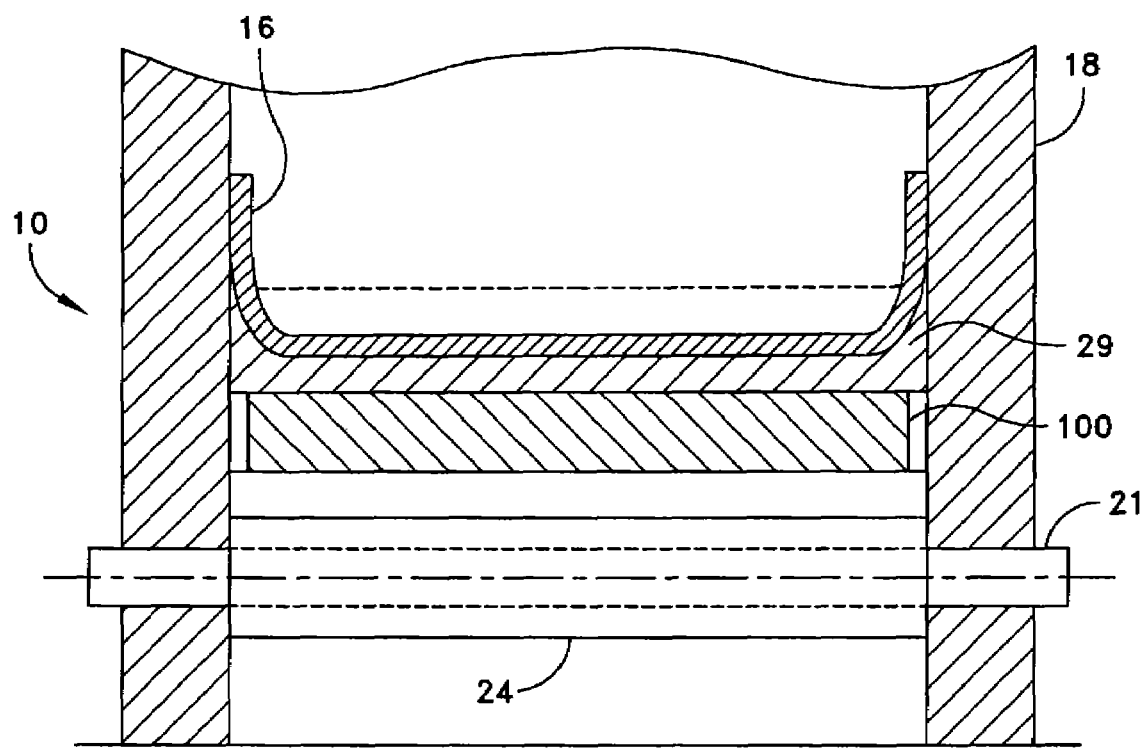
FIG. 6 depicts a cross-sectional view of the test apparatus of the present invention with the view taken along reference line 6-6 of FIG. 1 and with the bladder of the apparatus pressurized with the extrusion seal in place for maximum pressure.
Figure 7:
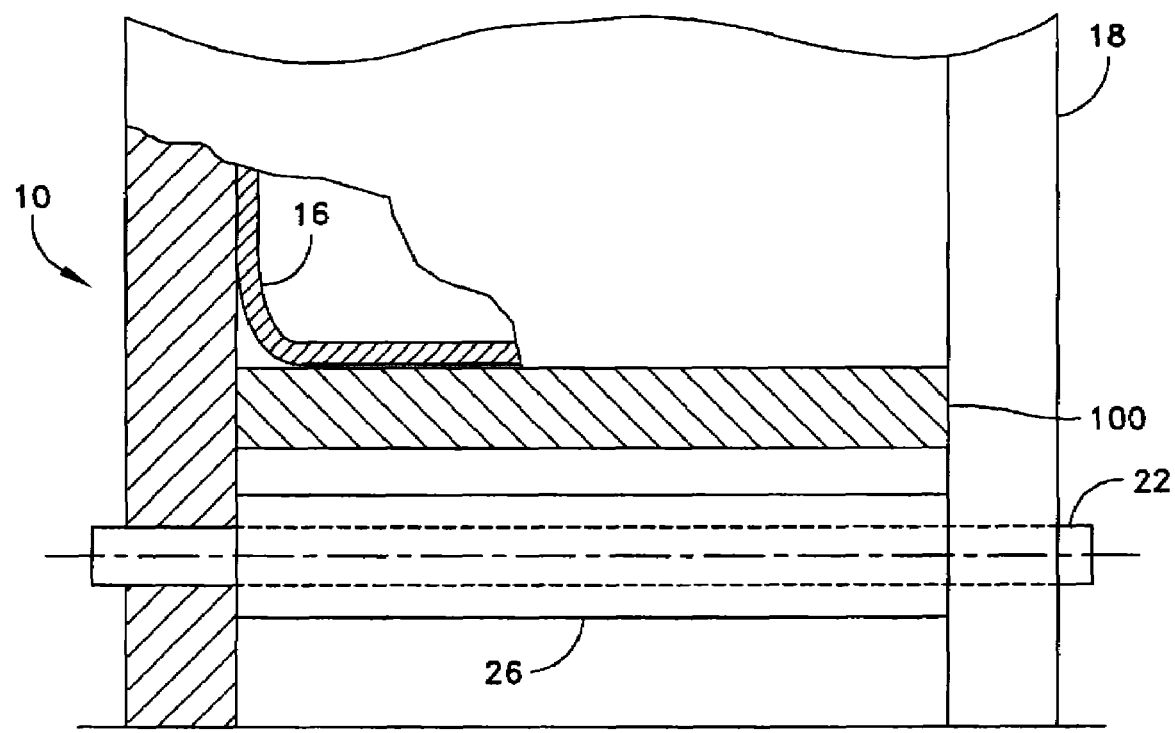
FIG. 7 depicts an alternate cross-sectional view of the test apparatus of the present invention with the view taken along reference line 7-7 of FIG. 1 and with the bladder of the apparatus pressurized without the extrusion seal in place and at a lesser pressure than the pressure depicted in FIG. 6.
Figure 8:
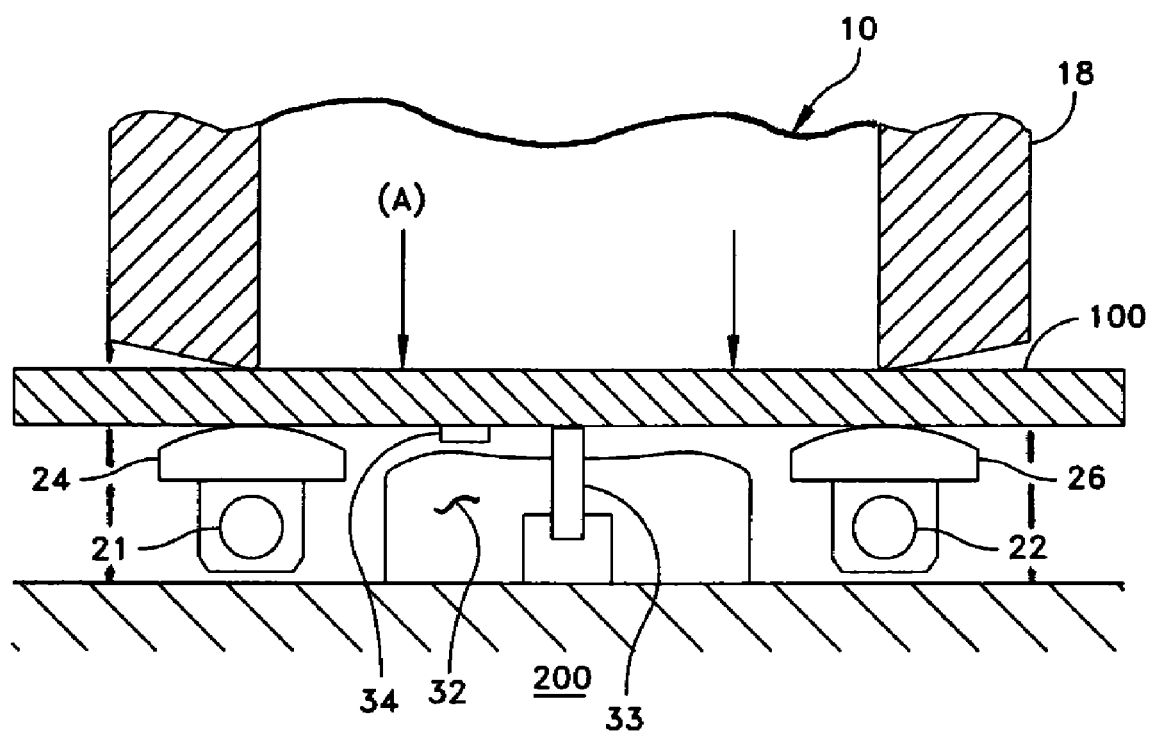
FIG. 8 depicts a snubber, strain gage and a switch placed on a surface for contact activation, deflection measurement and deflection mitigation by the test apparatus of the present invention.

As shown in FIG. 2 and FIG. 6, the extrusion seal 29 is a flexible seal with a reinforced lip edge. As shown in the figures, the extrusion seal 29 is capable of directing the volumized bladder 18 to apply pressure to the composite beam 100 rather than extruding around the support feet 24 and 26. FIG. 7 depicts the bladder fully pressurized As shown in FIG. 8, a snubber 32 may be added to mitigate deflection or catastrophe break of the composite sandwich beam 100 on the feet 24 and 26 or other associated parts of the test apparatus 10. The high durometer rubber snubber 32 can contain a switch 33 that inactivates a pump (not shown) or activates a valve (not shown) to shut off the supply to the pressure fitting 30, 46, 53 and 64. The bladder 16 should not expand further in direction "A" when the pump is off or the supply is cut off to the pressure fittings 30, 46, 53 and 64.

A strain gage 34 can be positioned on the composite sandwich beam 100 for remote and/or instantaneous measurements during pressure testing. The snubber 32 and switch 33 are preferably set on a stable surface 200 beneath the test apparatus 10. Deflection measuring devices can also be incorporated in and around the snubber 32 to contact the composite sandwich beam 100.

Figure 9:
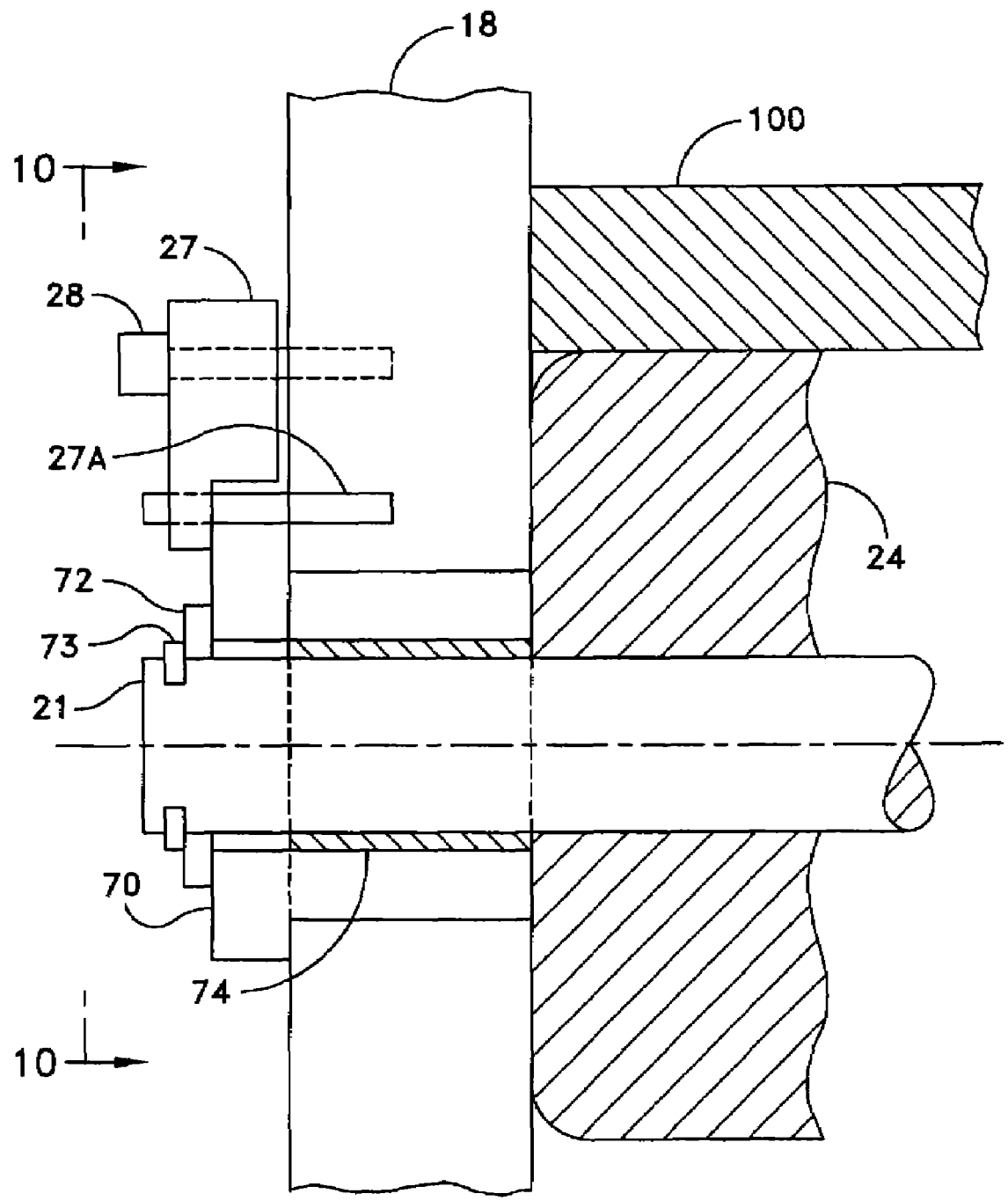
FIG. 9 depicts a cross-sectional view of a bushing and support feet arrangement of the apparatus of the present invention.

As shown in FIG. 9, an indexor clamp 27 and indexor bolt 28 will retain a pre-positioned bushing 70 in the box enclosure 18. Although not all shown in FIG. 1, each indexor clamp 27 and indexor bolt 28 will typically be provided for each bushing 70. The vernier bushings 70 are positioned using index marks and/or an indexor pin 27A to hold and position the composite sandwich beam 100. The bushing 70 is held within the box enclosure 18 by washers 72 and secured with snaprings 73, spiral rings, or any other attachment means known to those skilled in the art. The vernier bushing 70 encompasses a journal or roller bearing 74 for minimal rotational pin friction. The journal bearings 74 and the vernier bushings 70 secure and support each pin 21 and 22. The pins 21 and 22 support the feet 24 and 26 with the bushings providing vertical adjustment and hold the composite sandwich beam 100 in contact with the face of the bladder 16.

Figure 10:
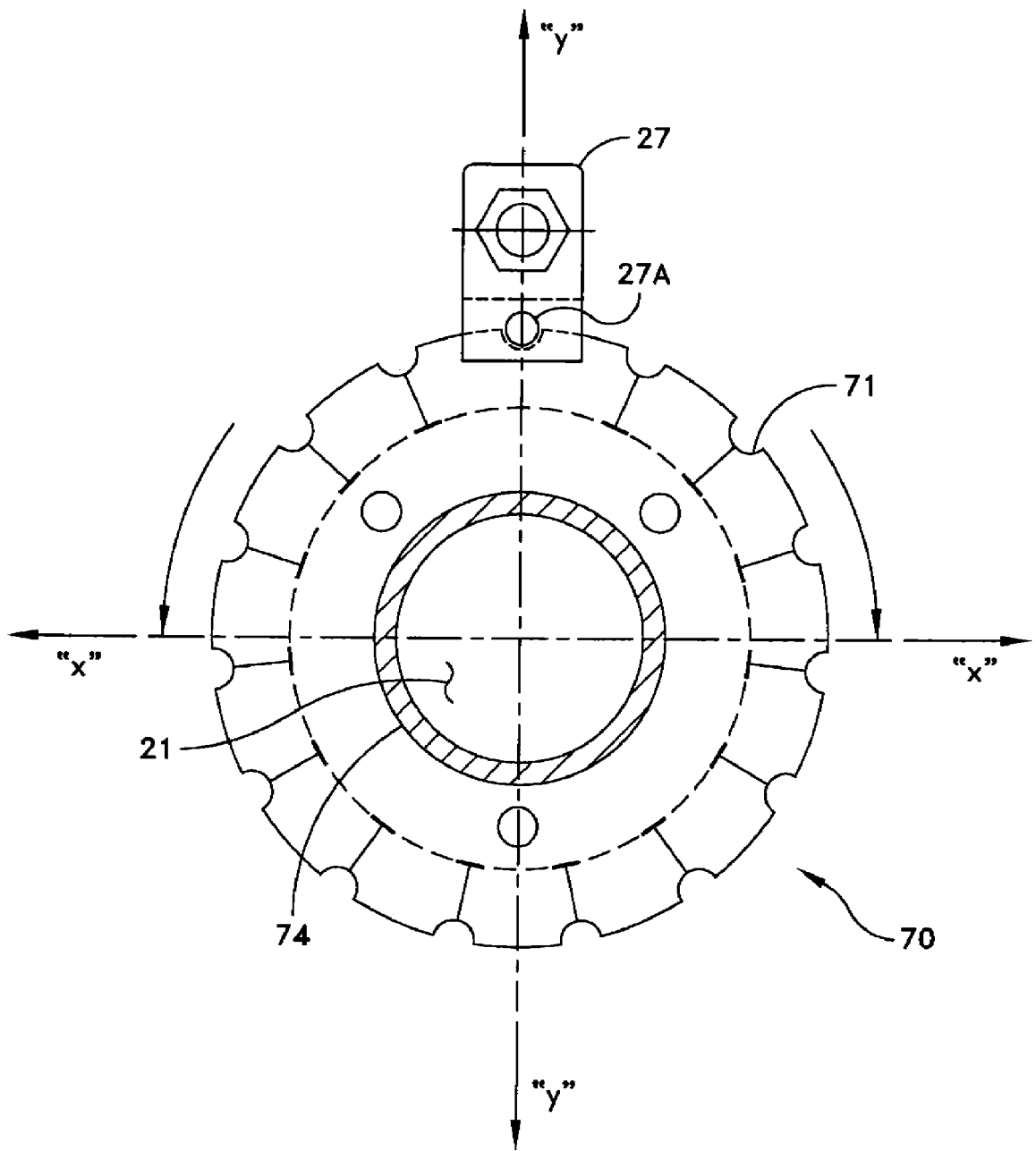
FIG. 10 depicts an end view of a notched vernier bushing with the view taken from reference line 10-10 of FIG. 9.

As shown in FIG. 10, the vernier bushing 70 with any offset may be rotated in either direction and held in position by the indexor clamp 27 using index marks and/or indexor pin 27A to position the pins 21 (or pin 22—not shown in the figures. The bushing 70 may include notches 71 to move the pins 21 and 22 in increments along an "x" and/or "y" horizontal/vertical axis plane perpendicular to the pins moving the feet 24 and 26 vertically permitting the composite sandwich beam 100 to contact the bladder 16. All offset bushings on the same positioning pins 21 and 22 must be rotated together in the same direction and position to maintain the pins on axis parallel to the bushing holes in the enclosure 18. The pins 24 and 26 will move in the x-y direction in a plane perpendicular to the bushing holes in the enclosure 18 when vertically adjusted with the bushings. To provide equal and opposite x-x positioning with the two separate pins, the two bushings on one pin should be rotated in equal and opposite directions of the bushings on the other pin providing equal y-y adjustments. Bushings may be rotated separately only if the pins are not in place.

Figure 11:
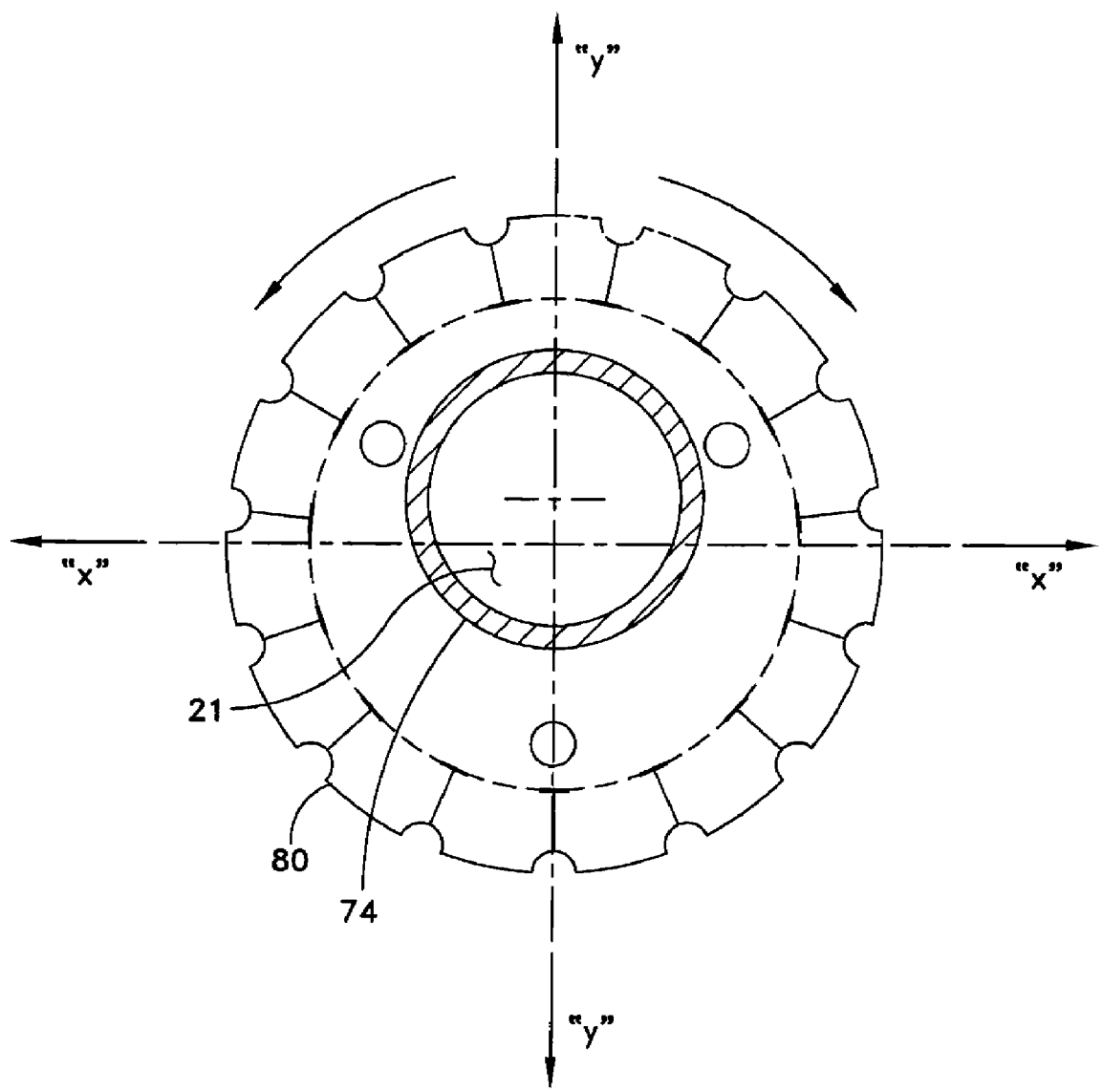
FIG. 11 depicts an end view of a first variant of a vernier bushing with a large offset.
Figure 12:
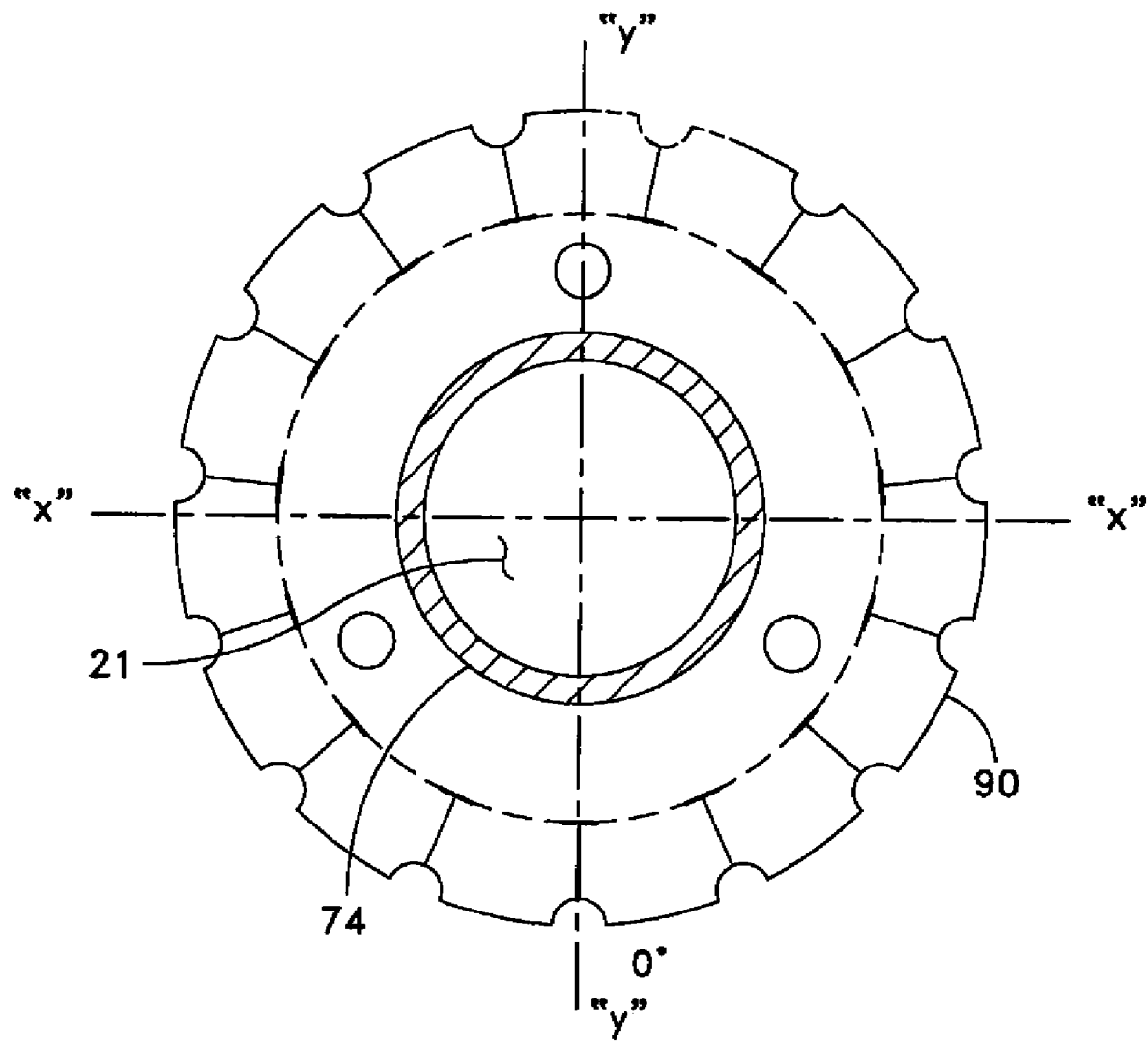
FIG. 12 depicts an end view of a second variant of a bushing with a concentric rotation.
Figure 13:
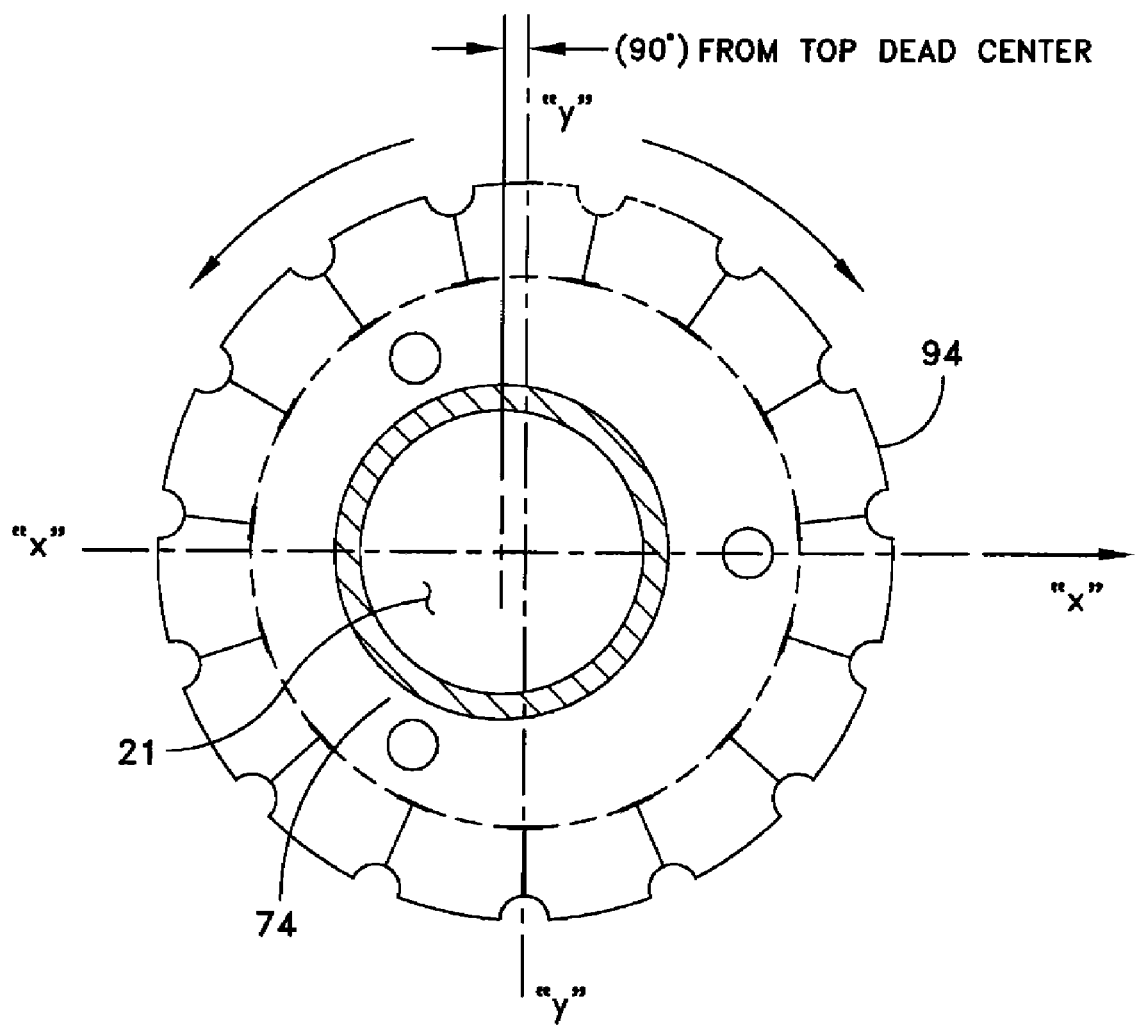
FIG. 13 depicts an end view of a third variant bushing with a small offset.

As shown in FIG. 11, a first variant vernier bushing 80 with a large offset is used to adjust the pin 21 and 22 in a varying position when rotated in either direction. The location of the journal or roller bearing 74 may be concentric (no offset) within a second variant vernier bushing 90 as shown in FIG. 12 and not adjustable. A small offset is shown with a third variant vernier bushing 94 in FIG. 13. With a large offset, the journal 74 and the first variant vernier bushing 80 are never concentric with each other. Even with a small offset, the journal 74 and the third variant vernier bushing 94 are also never concentric with each other. In both non-concentric and offset variants; rotation of the bushing moves the support feet along the "x" and "y" axis; thereby, altering hydraulic testing to impact slightly different areas 101 of the composite beam 100. Only the second variant bushing 90 is concentric with the journal 74.

The vertical height dimension of an example foot relative to the axis of the pin 21 in the feet may be manufactured in varying height sets to accommodate composite sandwich beams of different thicknesses. This would be accomplished in conjunction with adjusting the pin and bushing sets in the enclosure. A center of gravity of the feet 24 and 26 below the axis of the pins 21, 22 would ensure the top surface remains level with the composite sandwich beam 100 during assembly.

Figure 14:
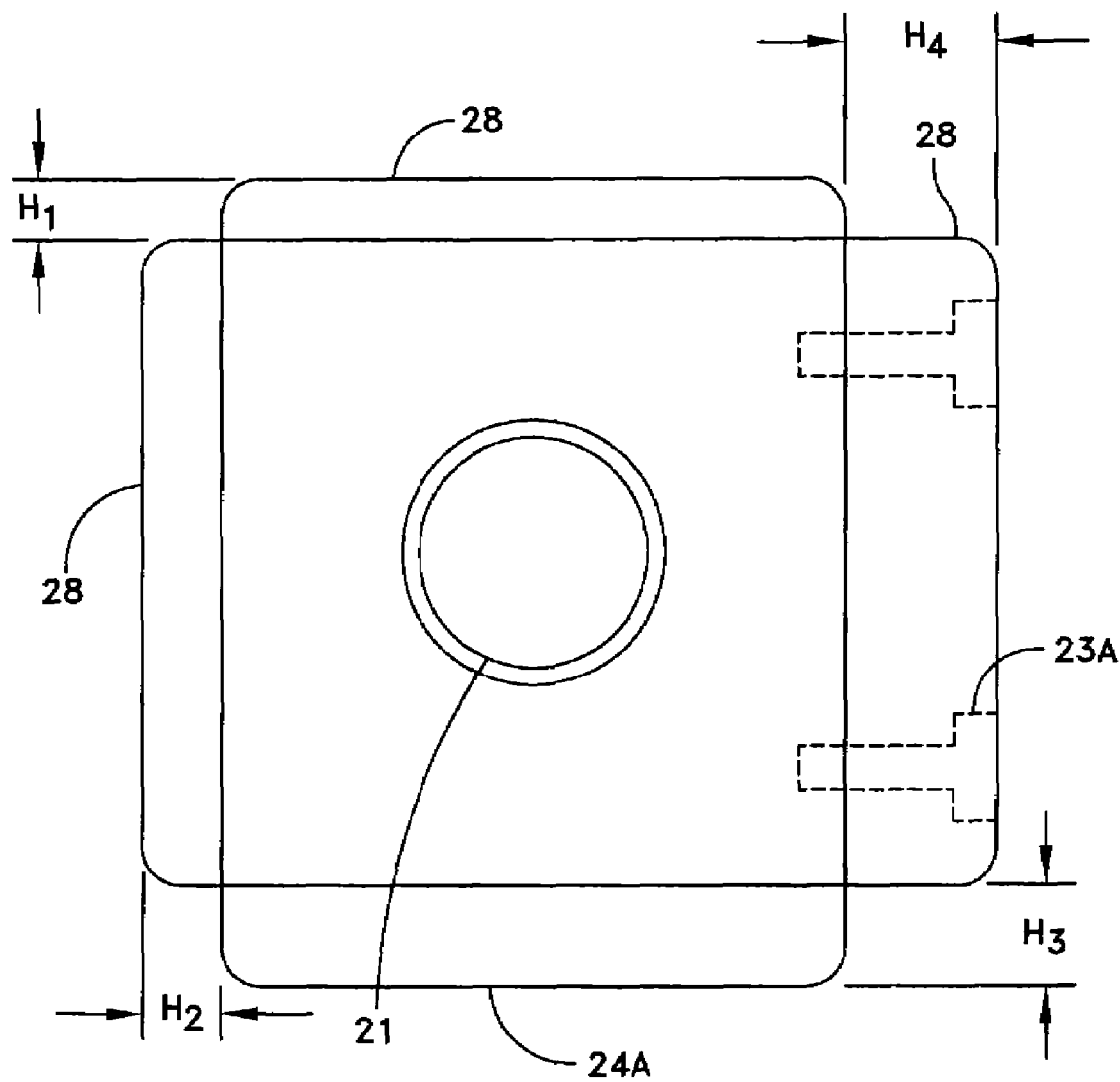
FIG. 14. depicts a first variant of the support feet of the present invention with an end view of the support feet.

Shimming on top of surfaces of the feet is a further adjustment option. Using two, three or four sides of basically square cross-sectioned feet there would accommodate large varying thicknesses of composite sandwich beams. More specifically and as shown in FIG. 14, a shim 28 of varying thickness can be attached to a rectangular first variant foot 24A. The shim 28 may be attached by flush-mounted bolting 28A, gluing, or other attachment means known to those skilled in the art. Also, each shim 28 can be rounded at the ends of the shim for case of movement. Another first variant foot 26A is similar in design and function to the first variant foot 24A but is not shown in the figure.

It will be understood that many additional changes in details, materials, steps and arrangement of parts which have been described herein and illustrated in order to explain the nature of the invention, may be made by those skilled in the art within the principle and scope of the invention as expressed in the appended claims.

What is claimed is:

1. A test apparatus for determining shear strength of an insertable and removable composite sandwich beam as a test piece, said apparatus comprising:
   an enclosure with a first aperture at a first end and a second aperture at a second end with a cutout along at least one side of said enclosure with the cutout extending from the second end partially to the first end wherein the cutout allows removable and insertion of the composite sandwich in said enclosure;
   a bladder sized to be insertable through the first aperture and expandable to create a volume within said enclosure with said bladder including a bladder flange integral to and extending outward from a first end of said bladder and to said at least one side of said enclosure;
   a blind flange mechanically attachable to the first end of said enclosure and said bladder flange such that said blind flange is capable of securing said bladder flange to said enclosure;
   at least one support platform for the insertable and removable composite sandwich beam, said support platform sized to be positioned at an open end of a perimeter of the cutout;
   at least one pressure fitting fluidly connected to said bladder through said blind flange, said pressure fitting capable of fluidly attaching to a pressure source to pressurize said bladder; and
   at least one drain fitting fluidly connected to said bladder for draining said bladder;
   wherein said bladder once filled to a predetermined pressure by way of said pressure fitting imparts a measurable hydrostatic load to the insertable and removable composite sandwich beam as a result of a constraining action by said enclosure and said blind flange during the filling action of said bladder.

2. The test apparatus of claim 1 further comprising fixtures capable of securing said support platform to said enclosure with said fixtures capable of being removed to allow removal of said support platform and the insertable and removable composite sandwich beam after measurement of the hydrostatic load to the composite sandwich beam.

3. The test apparatus of claim 2 wherein each of said fixtures is a pin.

4. The test apparatus of claim 3 further comprising a switch positionable on a side of said support platform opposite said bladder wherein said switch is capable of shutting down a supply from the pressure source once the insertable and removable composite sandwich beam bends to activate said switch.

5. The test apparatus of claim 4 further comprising a rubber snubber capable of mitigating deflection of the composite sandwich beam.

6. The test apparatus of claim 3 wherein said enclosure is an elongated box-like rectangular structure.

7. The test apparatus of claim 6 further comprising an extrusion seal positioned at a perimeter of the cutout.

8. The test apparatus of claim 7 further comprising at least one bushing adjacent to and in rotational contact for each said pin.

9. The test apparatus of claim 8 wherein said bushing includes notching as indexing marks around a perimeter of said bushing with said notching capable of securing rotation of said bushing by indexors wherein the insertable and removable composite sandwich beam and said support platform on said bladder are impacted when said notching position is altered.

10. The test apparatus of claim 9 wherein said bushing rotates in said enclosure in a journal bearing wherein an intersection location of said journal bearing along a plane of said bushing determines a positionable contact with and positioning of said pins to impact said support platform and the insertable and removable composite sandwich beam.

11. The test apparatus in accordance with claim 10 wherein said support platform is a four-sided elongated block capable of attaching to shims along sides of said four-sided elongated block to vary positioning of the insertable and removable composite sandwich beam.

12. The test apparatus of claim 6 wherein said rectangular structure includes at least one reinforced section of thickened material encompassing said structure perpendicular to a longitudinal axis of said structure.

13. The test apparatus of claim 12 further comprising an extrusion seal positioned at a perimeter of the cutout.

14. The test apparatus of claim 13 further comprising at least one bushing adjacent to and in rotational contact for each of said pins.

15. The test apparatus of claim 14 wherein said bushing includes notching as indexing marks around a perimeter of said bushing with said notching capable of securing rotation of said bushing by indexors wherein the insertable and removable composite sandwich beam and said support platform on said bladder are impacted when said notching position is alternated.

16. The test apparatus of claim 14 wherein said bushing rotates in said enclosure in a journal bearing along a plane of said bushing determines a positionable contact with and positioning of said pins to impact said support platform and the insertable and removable composite sandwich beam.

17. A test apparatus for determining shear strength of an insertable and removable composite sandwich beam as a test piece, said apparatus comprising:
   an enclosure with a first aperture at a first end;
   a bladder sized to be insertable through the first aperture and expandable to create a volume within said enclosure;
   at least one support platform for the insertable and removable composite sandwich beam, said support platform sized to be positioned and secured at the first aperture;

at least one pressure fitting fluidly connected to said bladder through said enclosure, said pressure fitting capable of fluidly attaching to a pressure source to pressurize said bladder; and at least one drain fitting fluidly connected to said bladder through said enclosure for draining said bladder;

wherein said bladder once filled to a predetermined pressure imparts a measurable hydrostatic load to the insertable and removable composite sandwich beam as a result of a constraining action by said enclosure during the filling action of said bladder.

18. The test apparatus of claim 17 further comprising an extrusion seal positioned at a perimeter of the first aperture.

19. The test apparatus of claim 18 further comprising a pin capable of securing said support platform to said enclosure and at least one bushing adjacent to and in rotational contact with each said pin.

20. The test apparatus of claim 17 wherein said enclosure is tubular along a longitudinal axis of said enclosure and includes a larger diameter section at the firs tend and at a second end of said enclosure.

* * * * *